United States Patent [19]

Geiger et al.

[11] Patent Number: 5,035,999

[45] Date of Patent: Jul. 30, 1991

[54] AMINOLUCIFERIN DERIVATIVES, PROCESSES FOR THE PRODUCTION THEREOF AND THEIR APPLICATION IN THE DETERMINATION OF ENZYME ACTIVITIES

[76] Inventors: Reinhard Geiger, Eisenhartstr. 6, D-8000 Müchen 60; Werner Miska, Haylerstr. 8, D-8000 München 50, both of Fed. Rep. of Germany

[21] Appl. No.: 254,932

[22] PCT Filed: Jan. 14, 1988

[86] PCT No.: PCT/EP88/00024

§ 371 Date: Aug. 18, 1988

§ 102(e) Date: Aug. 18, 1988

[87] PCT Pub. No.: WO88/05434

PCT Pub. Date: Jul. 28, 1988

[30] Foreign Application Priority Data

Jan. 14, 1987 [DE] Fed. Rep. of Germany ....... 3700908

[51] Int. Cl.$^5$ .................. C07D 277/68; C07D 417/04
[52] U.S. Cl. ........................................ 435/23; 435/24; 536/24; 548/178; 530/330; 530/331
[58] Field of Search ................ 548/178; 530/330, 331; 536/24; 435/23, 24

[56] References Cited

FOREIGN PATENT DOCUMENTS 0024525 3/1981 European Pat. Off. .
02667 5/1987 PCT Int'l Appl. .

OTHER PUBLICATIONS

White et al, JACS, vol. 88, No. 9 (5-1960), pp. 2015-2019.

*Primary Examiner*—Richard L. Raymond
*Attorney, Agent, or Firm*—Lowe, Price, LeBlanc & Becker

[57] ABSTRACT

The invention relates to D-aminoluciferin derivatives of the general formula I

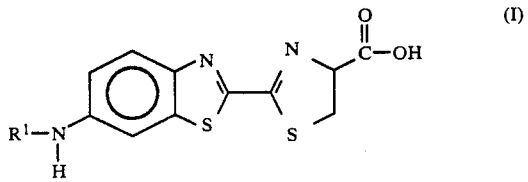

wherein $R^1$ represents a L-amino acid or peptide radical having up to 10 L-amino acid moieties said radical being bound via the (terminal) carboxyl group in the form of an amide and the free amino group thereof is optionally be protected by a common protecting group, or wherein $R^1$ represents a monosaccharide or disaccharide radical.

Said aminoluciferin derivatives can be cleaved by enzymes giving free aminoluciferin which can be determined luminometrically.

The invention relates also to the use of said aminoluciferin derivatives for determining enzyme activities as well to a process for producing said aminoluciferin derivatives.

13 Claims, No Drawings

AMINOLUCIFERIN DERIVATIVES, PROCESSES FOR THE PRODUCTION THEREOF AND THEIR APPLICATION IN THE DETERMINATION OF ENZYME ACTIVITIES

The invention relates to aminoluciferin derivatives, processes for their production and to the use thereof for the determination of enzyme activities.

In the common analytical methods for determining enzyme activities, for instance in a biological material, fluorogenic and chromogenic substrates are used from which a leaving group can be cleaved off with the help of the enzymes.

Such a leaving group can be for instance a dye. The dyes which are developed in the course of said indicator reaction can be measured photometrically. Therefore it is possible to determine their concentration and to deduct from the data obtained informations with respect to the enzymatic activity, see "Methods of Enzymatic Analysis, Verlag Chemie, Vol. 1-11, Weinheim, BergstraBe (1984), editor H. U. Bergmeyer.

As an example for such a leaving group the concentration of which can be photometrically determined the following group is mentioned:

In case one uses the above mentioned fluorogenic substrate one can then photometrically determine the leaving group. As an example for the leaving group of a fluorogenic substrate the following group can be mentioned:

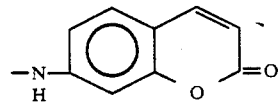

With the known substrates it is possible to determine or measure, respectively, enzyme concentrations down to about 5 ng per test. In this case it is referred to the enzymatic activity (U). From the specific activity (U/mg) the amount of enzyme can be deducted.

The enzymatic activity (U) is defined as $\mu$mol/min; mainly measured at 25° C. Said enzymatic activity is also named catalytic activity and is expressed according to SI-units as Katal (kat=mol/s). The catalytic concentration (catalytic activity per volume) is expressed as kat/l.

By the present invention there are provided new substrates. With the help of said substrates it is possible to surprisingly increase the sensitivity of the analytical methods mentioned above in order to determine enzyme activities. It is for instance possible to determine enzyme concentrations down to about 10 to 100 fg per test. This means that the detection limit has been lowered. The sensitivity depends of course on the enzyme investigated and the substrate used.

It is common to all substrates as provided according to the present invention that the enzymes tested are capable of cleaving off or liberating, respectively, D-aminoluciferin of the following formula V

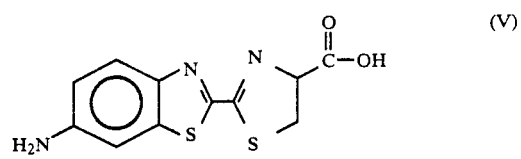

from said substrates.

Said aminoluciferin (V) therefore represents a leaving group as it has been explained in the beginning.

The liberated aminoluciferin can be luminometrically detected even in smallest concentrations. For this purpose said aminoluciferin is reacted with the enzyme luciferase of the fire-fly Photinus pyralis or of the fire-fly Photinus plathiophthalamus or of the luciferase of other species or chemically or genetically modified luciferases in the presence of ATP+MgCl$_2$. In the course of said reactions photones are emitted; i.e. in the course of the reaction with the enzyme of the fire-fly Photinus pyralis at 605 nm and in the course of the reaction with the enzyme of the fire-fly Photinus plathiophthalamus at 549 or 570 nm, or wavelength corresponding to the used liciferin/luciferase system, respectively. The emission at 549 nm takes place if the enzyme originates from the dorsal organ of the fire-fly mentioned whereas the emission at 570 nm takes place if the enzyme originates from the ventral organ.

The above described is a bioluminescence. The light emitted is measured luminometrically.

For further details it is referred to the following literature: "Luminometry" by K. Wulff in "Methods of Enzymatic Analysis", Vol. I (editor: H. U. Bergmeyer), pages 340-368, Verlag Chemie, Weinheim, BergstraBe (1983) and Journal of the American Chemical Society 88, 2015-2018, 1966 by E. H. White et al.

By the data obtained the enzyme concentration of the investigated enzyme can be determined. The exact execution of said determination with the help of a "bioluminescence cocktail" as well as the calibration are explained further in the examples.

The present invention relates therefore to D-aminoluciferin derivatives of the general formula I

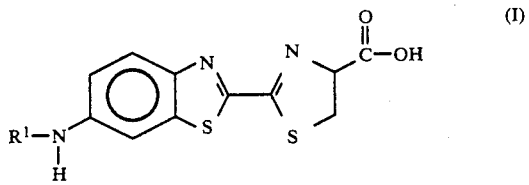

wherein $R^1$ represents a L-amino acid radical or a peptide radical having up to 10 L-amino acid moieties, said radical being bound via the (terminal) carboxyl group as an amide and the free amino group(s) of which are optionally protected by a common protecting group, or $R^1$ represents a monosaccharide or disaccharide radical.

The amino acid radicals of the present invention are bound via the carboxyl group to the amino group of the luciferin in the form of an amide. The amino acids possess L-configuration. The amino group is bound to the $\alpha$-position of the carboxyl group.

The amino acid radical $R^1$ is derived from common amino acids, for example from amino acids having an unpolar group, such as glycine, alanine, valine, leucine, isoleucine, proline and phenylalanine, amino acids having non-ionized but polar groups, such as tyrosine, tryptophan, serine, threonine, cysteine, cystine, methionine, hydroxyproline, allothreonine, homoserine and homocysteine, acidic amino acids (amino dicarboxylic acids), such as aspartic acid and glutaminic acid (and also the amides thereof, i.e. asparamide and glutamine), and basic amino acids, for instance lysine, arginine and histidine.

The radical $R^1$ can also be derived from hydroxylysine, α-aminoadipinic acid, ornithine, citrulline, homoarginine, α,ε-diaminopimelic acid, γ-amino butyric acid and phenylserine.

The amino acid radical corresponds preferably to the following general formula II $$\begin{array}{c} R^3 \ H \ O \\ | \ \ | \ \ \| \\ H-N-C-C- \\ | \\ R^2 \end{array}$$ (II)

wherein $R^3$ represents a hydrogen atom or a common protecting group and
$R^2$ is —H, —CH$_3$, —CH$_2$OH, —CH(OH)CH$_3$, —CH(CH$_3$)$_2$, —CH$_2$CH(CH$_3$)$_2$, —CH(CH$_3$)CH$_2$CH$_3$, —CH$_2$COOH, —CH$_2$CONH$_2$, —CH$_2$CH$_2$COOH, —CH$_2$CH$_2$CONH$_2$, —CH$_2$CH$_2$CH$_2$CH$_2$NH$_2$, —CH$_2$C$_6$H$_4$OH, —CH$_2$C$_6$H$_5$,

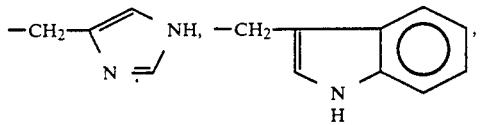

—CH$_2$SH, —CH$_2$CH$_2$CH$_2$—NH—C(=NH)—NH$_2$ or —CH$_2$CH$_2$SCH$_3$.

Proline and hydroxy proline radicals are also preferred radicals.

Any common protecting group can be used as amino protecting group. Acetyl, benzoyl, tosyl, benzyloxycarbonyl, tert.-butyloxycarbonyl, succinyl and methoxysuccinyl protecting groups are preferred.

The peptide radical of the compounds of the present invention of the general formula I consists out of any of the amino acids mentioned above and contains up to 10 of such amino acid moieties. The peptide radical is bound via the terminal carboxylic group to the basic luciferin unit.

Said peptide radical contains preferably 5 amino acid moieties. A peptide radical having 2 amino acid moieties is most preferred.

In case the radical $R^1$ of the compounds of the present invention of the general formula I represents a monosaccharide radical said radical is derived from a common hexose or pentose, such as glucose, galactose, mannose, fucose, ribose, desoxyribose, fructose and lactose. Said radicals are bound via $C^1$ to the basic luciferin unit.

The disaccharide radical consists out of the mentioned sugar radicals.

The invention relates also to a process for producing the D-aminoluciferin derivatives of the general formula I. Said process is characterized in that one a) in order to produce compounds of the general formula I wherein $R^1$ represents a L-amino acid or peptide radical, reacts a N-protected amino acid or peptide, respectively, which corresponds to the amino acid or peptide radical, respectively, as defined above, either with 2-cyano-6-aminobenzothiazole of the formula III

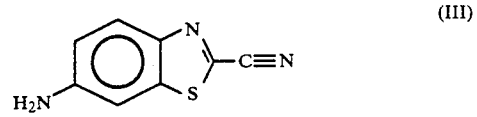

to give a compound of the general formula IV

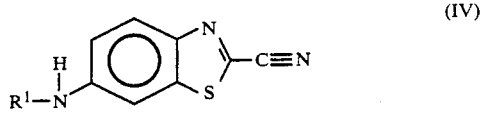

wherein $R^1$ has the meanings given above, and reacts the thus obtained compound of the general formula IV with D-cysteine to give a compound of the general formula I and optionally cleaves off the amino protecting group(s) in a common manner or with D-aminoluciferin the carboxyl group of which is protected by a common protecting group of the formula Va

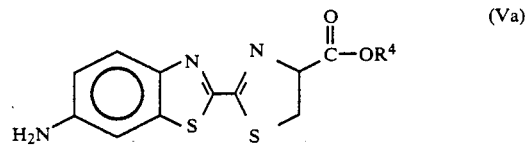

wherein $R^4$ represents a common protecting group for the carboxyl group and removes the protecting group for the carboxyl group as well as the protecting group(s) of the amino group(s), if present, in a common manner or b) in order to produce compounds of the general formula I wherein $R^1$ represents a monosaccharide or disaccharide radical, reacts aminoluciferin of the formula Va the carboxyl group of which is protected with the corresponding Br$^1$-monosaccharide or Br$^1$-disaccharide and cleaves off then the protecting group of the carboxyl group.

The compound III is reacted in the presence of phosphorustrichloride to give the compound IV. The reaction is preferably performed in a reaction inert absolute solvent, such as THF, DMF or DMSO, preferably in anhydrous pyridine and by agitating at low temperatures, preferably at −5° C. to −20° C. Said reaction is called the phospho-azo-method.

The compounds IV can also be produced starting from the compound III according to the mixed anhydride method.

In order to perform said method the N-protected amino acid or the N-protected peptide is dissolved in a reaction inert solvent, preferably absolute pyridine, THF, DMF or DMSO. Chloroformic acid isobutylester and a tertiary amine, preferably triethylamine, are added to said solution. The compound III is then added to said solution.

The reaction of the compound IV with D-cysteine to give the aminoluciferin is preferably performed in water which is saturated with $N_2$.

In case one starts out from a protected aminoluciferin of the formula Va, then the amino acid (or the peptide) can be introduced as well either via the phospho-azo-method or via the mixed anhydride method. The reaction conditions correspond to those given above.

The amino protecting groups can be removed in a common manner, for instance by a catalytical hydrogenation employing for instance palladium-on-charcoal in methanol, by a hydrazinolysis or by a mild acid treatment.

Methyl, ethyl, tert. butyl, benzyl and phenacyl groups are preferably used as protecting groups for carboxylic groups. They can be removed in a common manner, for instance by a basic catalyzed hydrolysis. The benzyl ester can also be reacted with palladium-on-charcoal. The carboxyl group is preferably protected by converting it to the methyl ester. Said ester is then cleaved into the free acid and methanol, preferably by a treatment with carboxyl esterase.

The amino acid (or the peptide) can therefore be bound to 2-cyano-6-aminobenzothiazole (III) or to aminoluciferin according to two methods, i.e. via the phospho-azo-method and via the mixed anhydride method. Said reactions are further illustrated by the following schemes 1 and 2.

Scheme 1

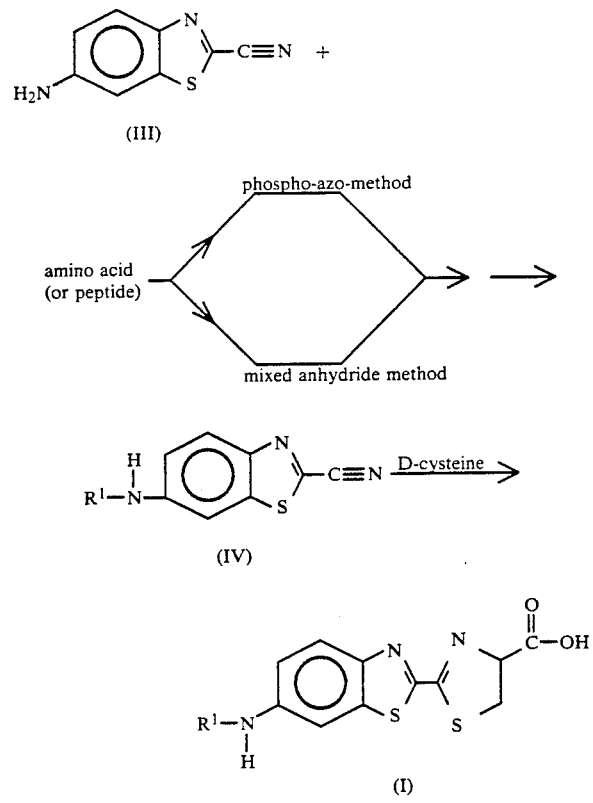

Scheme 2

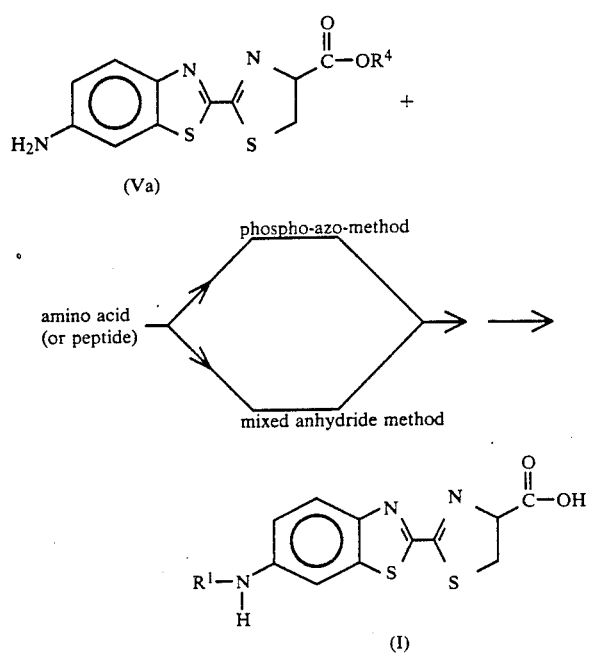

The aminoluciferin is produced as pointed out below according to a process described in the literature:

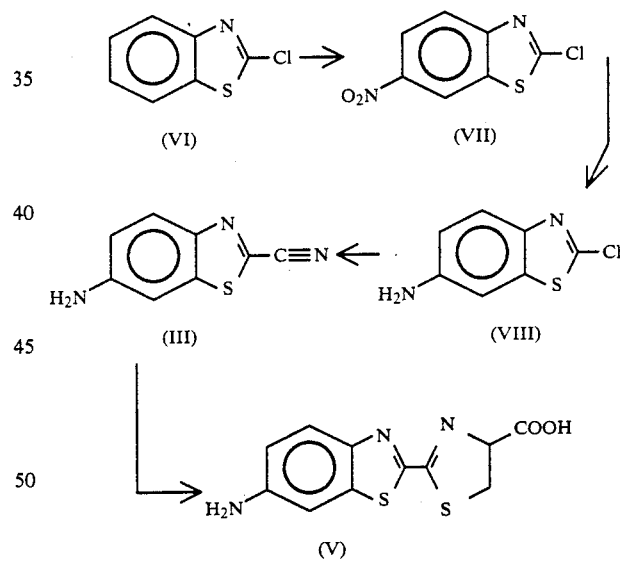

VI: available on the market;
VII and VIII: obtained according to Katz, J. Am. Chem. Soc. 73 (1951) 4007;
III and V: obtained according to White et al., J. Am. Chem. Soc. 88, (1966) 2015.

It has to be emphasized that the free aminoluciferin as well as the amino acid derivative ($R^1$ has the meanings given above) possess D-configuration.

The production of the compounds of the present invention of the general formula I wherein $R^1$ represents a monosaccharide or disaccharide radical starts out also from the aminoluciferin. The carboxyl group of the aminoluciferin is protected by methylating it for instance. Said protected compound is then reacted with a Br$^1$-monosaccharide or Br$^1$-disaccharide. Then the methyl group is cleaved off with carboxyl esterase.

The compounds of the present invention can be used in order to measure the enzyme activity of rather different enzymes. Said enzymes have to be able to liberate aminoluciferin V from the compounds of the present invention, i.e. they have to be capable of cleaving off the radical R$^1$. Said enzymes have therefore to cleave the amide bond between the aminoluciferin and the amino acid radical.

A man skilled in the art knows that enzymes are more or less specific with respect to the amide bond and with respect to the amino acid. Some enzymes are therefore for instance only capable of cleaving the amide bond of very specific amino acids.

In case one wants to determine a given enzyme it is appropriate to proceed as follows:

In case it is known that said enzyme is only capable of cleaving off the amide bond of specific amino acids then such an aminoluciferin of the present invention is used which carries as the radical R$^1$ said amino acid unit with which the enzyme specifically reacts.

Further down the luminometric test used according to the present invention is illustrated:

One uses a "bioluminescence-cocktail" for said luminometric test having the following composition:

---
30 mmol/l HEPES (N-2-hydroxyethylpiperazine-N'-2-
  ethane sulfonic acid)
6 mmol/l MgCl$_2$
6 mmol/l ATP
0,5 mmol/l EDTA
80 μmol/l DTT (Dithiothreitol)
1 μg luciferase (of the fire-fly *Photinus pyralis*
  or *plathiophthalamus* or others)
complete volume: 0.4 ml; pH 7.75
---

In order to determine an unknown enzyme concentration it is necessary to generate a calibration curve. In order to do so solutions having different, however known concentrations of aminoluciferin are reacted with a certain and known amount of the bioluminescence cocktail. Then the number of the light pulses for a period of 10 sec are measured.

A certain number of light pulses is therefore related to a certain concentration of aminoluciferin. During the determination of an unknown enzyme activity a certain amount of aminoluciferin is liberated from the compounds of the present invention of the general formula I. Said amount of liberated aminoluciferin can be determined with the help of the luminometric test. It is then known which amount of aminoluciferin has been liberated. From said data the enzyme activity can be calculated.

In order to perform said luminometric test 0.1 ml of the sample to be tested is appropriately admixed with 0.14 ml of the bioluminescence-cocktail. Thereafter the light pulses are measured or counted, respectively, for a period of 10 sec.

There are now described the different tests for determining different enzyme activities.

EXAMPLE 1

Determination of chymotrypsin enzyme activity and of chymotrypsin-like enzyme activity, for instance in feces.

N$^α$-acetyl-L-phenyl-alanyl-amino-luciferin is used as compound of the present invention.

The following sample to be tested (test sample) is prepared:

0.90 ml buffer (0.1 mol/l triethanolamine, 0.02 mol/l CaCl$_2$, pH=7.8)
0.05 ml substrate solution (N$^α$-acetyl-L-phenylalanylaminoluciferin; 1 mmol/l in H$_2$O)

It is incubated at 25° C. for 5 min. Then 0.05 ml of a solution containing chymotrypsin are added.

After exactly 1 min 0.1 ml of the test sample are removed and admixed with 0.4 ml of the bioluminescence-cocktail described above. Thereafter the light pulses are measured for a period of 10 sec.

In said determination the N$^α$-acetyl-L-phenylalanine-amino-luciferin can be replaced by the same amount of N$^α$-acetyl-L-tyrosyl-amino-luciferin.

It is possible to determine with this test an amount of chymotrypsin down to 10 fg. By variations of the test conditions (incubation time during the test, reaction temperature) the detection limit can be shifted still further down.

EXAMPLE 2

Determination of trypsin enzymatic activity and trypsin-like enzymatic activity.

N$^α$-acetyl-L-arginyl-amino-luciferin is used as the compound of the present invention.

The test sample has the following composition:

0.75 ml buffer (0.2 mol/l triethanolamine, 0.02 mol/l CaCl$_2$; pH=7.8)
0.05 ml substrate solution (1 mmol/l N$^α$-acetyl-L-arginyl-aminoluciferin in H$_2$O)

It is incubated for 5 min at 25° C. Then 0.3 ml trypsin solution are added.

After exactly one minute 0.1 ml of the test sample are removed and admixed with 0.4 ml of the bioluminescence-cocktail, then the luminometric test as described above is performed.

It is possible to determine with said test an amount of trypsin down to 10 fg. Also in this case the detection limit can be shifted further down by varying the test conditions.

N$^α$-acetyl-L-arginyl-aminoluciferin can be replaced in said test by N$^α$-acetyl-L-lysyl-aminoluciferin.

Said test can also be used for determining kallikrein.

EXAMPLE 3

Determination of elastase and elastase-like activity.

N$^α$-acetyl-L-alanyl-aminoluciferin is used as the compound of the present invention.

The test sample has the following composition:

0.85 ml buffer (0.2 mol/l triethanolamine; pH=7.8)
0.05 ml substrate solution (1 mmol/l N$^α$-acetyl-L-alanylaminoluciferin in H$_2$O)

It is incubated for a period of 5 min at 25° C. Then 0.10 ml of a solution containing elastase are added.

After one minute 0.1 ml of the test sample is removed and admixed with 0.4 ml of the bioluminescence-cocktail described above. Thereafter the light pulses are measured for a period of 10 sec.

Said test is capable of determining an amount of elastase down to 10 fg.

PREPARATION EXAMPLES

1. Preparation of the aminoluciferin derivatives of the general formula I, wherein $R^1$ represents an amino acid radical or peptide radical.

a) Preparation via the phospho-azo-method starting from 2-cyano-6-aminobenzothiazole of the formula III 17.5 mg (0.1 mmol) 2-cyano-6-aminobenzothiazole (III) are dissolved at $-10°$ C. in anhydrous pyridine and admixed under stirring with 5 μl (0.056 mmol) phosphorus-trichloride. After 1 h at $-10°$ C. a suspension of 0.11 mmol protected amino acid or peptide in ice-cold pyridine are given to the reaction sample. It is allowed to slowly warm up to room temperature (RT). It is stirred 20 h at RT. Then pyridine is removed in vacuo and the residue is taken up in butanol (saturated with water), filtered and finally concentrated. The residue is taken up in a slow amount of water and purified via HPLC (solution A).

0.11 mmol D-cysteine are dissolved in water saturated with $N_2$. The pH is adjusted to 7.5 and it is purged with $N_2$. Then the solution A, which has been saturated with nitrogen before, is added and it is stirred 2 h under nitrogen at room temperature under the exclusion of light. Then the solution is concentrated and taken up in water/ethanol (50/50). After optionally removing the amino protecting group(s) in a common manner it is purified via HPLC.

b) Preparation via the mixed anhydride method starting from 2-cyano-6-benzothiazole of the formula III 0.135 mmol of the amino acid or the peptide, dissolved in absolute tetrahydrofurane (DMF or DMSO) are cooled down to $-15°$ C. Then the solution is admixed with 14 μl (0.1 mmol) triethyl amine and 13 μl (0.1 mmol) chloroformic acid-isobutylester. Then it is stirred 30 min at $-15°$ C. Then 17.5 mg (0.1 mmol) 2-cyano-4-amino-benzothiazole (III) in dimethylformamide (precooled) are added. It is allowed to slowly warm up to room temperature and stirred over night. Then the precipitated triethyl ammonium hydrochloride is filtered off, the filtrate is concentrated and the residue is taken up in a small amount of water. Then it is purified via HPLC (solution B).

0.1 mmol D-cysteine are dissolved in water which has been saturated with $N_2$. The pH is adjusted to 7.5 and it is continued to purge with $N_2$. To said solution the solution B, which has been saturated with nitrogen before, is added and it is stirred 2 h at room temperature under nitrogen and under the exclusion of light. Then the solution is concentrated. The residue is taken up in water/ethanol (50/50), the amino protecting group(s) are optionally cleaved off and it is purified via HPLC.

c) Preparation via the phospho-azo-method starting from the aminoluciferin of the formula V 0.05 mmol protected aminoluciferin (Va) (preferably the methyl ester thereof) are dissolved at $-10°$ C. in anhydrous pyridine and admixed under stirring with 2.5 μl (0.028 mmol) phosphorustrichloride. After 1 h at $-10°$ C. 0.055 mmol protected amino acid or protected peptide, suspended in ice-cold pyridine, are given to the reaction sample. It is allowed to slowly warm up to room temperature and it is stirred 20 h at room temperature (RT).

Then pyridine is removed in vacuo in a rotary evaporator and the residue is taken up in butanol saturated with water. It is then filtered and concentrated. The residue is taken up in a small amount of water, the protecting group of the carboxyl group (in case of the methyl ester with the help of carboxyl esterase) as well as the protecting group, if present, of the amino group(s) are removed and it is purified via HPLC.

d) Preparation via the mixed anhydride method starting from the aminoluciferin of the formula V 0.0135 mmol protected amino acid or protected peptide, dissolved in absolute tetrahydrofurane (DMF, DMSO), are cooled to $-15°$ C. The solution is then admixed with 1.4 μl (0.01 mmol) triethyl amine and 1.3 μl (0.01 mmol) chloroformic acid-isobutyl ester and it is stirred 30 min at $-15°$ C.

Then 0.01 mmol protected aminoluciferin V in dimethylformamide (pre-cooled) is added. It is allowed to warm up slowly to room temperature and it is stirred over night. Precipitated triethyl ammonium-hydrochloride is then filtered off, the filtrate is concentrated and taken up in a small amount of water and the protecting group of the carboxyl group as well as the protecting group(s) of the amino group(s), if present, are removed. Finally it is purified via HPLC.

The aminoluciferin derivatives mentioned further down can be prepared according to the methods of preparation mentioned above:

| | C | H | N |
|---|---|---|---|
| $N^\alpha$-acetyl-L-phenylalanyl-amino-luciferin analysis for $C_{22}H_{20}N_4S_2O_4$ (mw = 468.56) | | | |
| calculated: | 56.3% | 4.3% | 12.0% |
| found: | 56.2% | 4.3% | 12.1% |
| contents of amino acid: | | | |
| calculated: | 35.21% | | |
| found: | 34.15% | | |
| $N^\alpha$-acetyl-L-arginyl-amino-luciferin analysis for $C_{19}H_{23}N_7S_2O_4$ (mw = 477.58) | | | |
| calculated: | 47.7% | 4.8% | 20.5% |
| found: | 47.5% | 4.7% | 20.4% |
| contents of amino acid: | | | |
| calculated: | 36.43% | | |
| found: | 35.70% | | |
| $N^\alpha$-acetyl-L-tyrosyl-amino-luciferin analysis for $C_{22}H_{20}N_4S_2O_5$ (mw = 484.57) | | | |
| calculated: | 54.5% | 4.1% | 11.6% |
| found: | 54.6% | 4.0% | 11.6% |
| contents of amino acid: | | | |
| calculated: | 44.78% | | |
| found: | 43.54% | | |
| $N^\alpha$-acetyl-L-lysyl-amino-luciferin analysis for $C_{19}H_{23}N_5S_2O_4$ (mw = 449.56) | | | |
| calculated: | 50.7% | 5.1% | 15.6% |
| found: | 50.6% | 5.0% | 15.8% |
| contents of amino acid: | | | |
| calculated: | 32.48% | | |
| found: | 31.83% | | |
| $N^\alpha$-acetyl-L-alanyl-amino-luciferin analysis of $C_{16}H_{16}N_4SO_4$ (mw = 360.39) | | | |
| calculated: | 53.3% | 4.5% | 15.6% |
| found: | 53.2% | 4.5% | 15.6% |
| contents of amino acid: | | | |
| calculated: | 24.70% | | |
| found: | 23.96% | | |

The following compounds have been prepared according to the methods of preparation given above:

a) $N^\alpha$-Acetyl-L-phenylalanyl-L-arginylaminoluciferin ($C_{28}H_{32}N_8S_2O_5$ (mw=624,75))
b) $N^\alpha$-Methoxysuccinyl-L-alanyl-L-alanyl-L-valylaminoluciferin ($C_{27}H_{34}N_6{_2}SO_7$ (mw=618,74))
c) $N^\alpha$-Methoxysuccinyl-L-alanyl-L-alanyl-L-proly-L-valylaminoluciferin ($C_{32}H_{41}N_7S_2O_9$ (mw=731,85))
d) $N^\alpha$-Methoxysuccinyl-L-alanyl-L-alanyl-L-proly-L-phenylalanylaminoluciferin ($C_{36}H_{41}N_7S_2O_9$ (mw=779,90))
e) $N^\alpha$-Acetyl-L-alanyl-L-alanyl-L-alanylaminoluciferin ($C_{21}H_{26}N_6S_2O_6$) (mw=522,61))
f) $N^\alpha$-Acetyl-L-phenylalanyl-L-glycylaminoluciferin ($C_{24}H_{23}N_5S_2{_5}O$ (mw=525,61))
g) $N^\alpha$-Acetyl-L-glycyl-L-arginylaminoluciferin ($C_{21}H_{26}N_8S_2O_5$ (mw=534,62))
h) Pyroglutamyl-L-glycyl-L-arginylaminoluciferin ($C_{24}H_{29}N_9S_2O_6$ (mw=603,68))
i) Pyroglutamyl-L-phenylalanyl-L-leucylaminoluciferin ($C_{31}H_{34}N_6S_2O_6$ (mw=650,78))
j) Succinyl-L-alanyl-L-alanyl-L-prolyl-L-methionylaminoluciferin ($C_{31}H_{39}N_7S_3O_9$ (mw=707,87))
k) $N^\alpha$-Benzoyl-L-prolyl-L-phenylalanyl-L-arginylaminoluciferin ($C_{38}H_{41}N_9S_2O_6$ (mw=783.93))
l) $N^\alpha$-Tosyl-glycyl-L-prolyl-L-lysylaminoluciferin ($C_{31}H_{37}N_6S_3O_7$ (mw=701.87))
m) $N^\alpha$-Benzoyl-$\beta$-alanyl-glycyl-L-arginylaminoluciferin ($C_{29}H_{33}N_9S_2O_6$ (mw=667.77))
n) $N^\alpha$-Carbobenzoxy-L-valyl-glycyl-L-arginylaminoluciferin ($C_{32}H_{38}N_9S_2O_8$ (mw=740.84))
o) $N^\alpha$-Tosyl-glycyl-L-prolyl-L-arginylaminoluciferin ($C_{31}H_{37}N_9S_3O_7$ (mw=743.89))

The aminoluciferin derivatives mentioned above under a), g) and h) are preferably prepared according to the mixed anhydride method.

The following Table shows which enzymes can be determined by which of the aminoluciferin derivatives of the present invention. It is mentioned which enzymes are capable to cleave the aminoluciferin derivative which has been used as a substrate to give the free aminoluciferin as well as the corresponding amino acid or the corresponding peptide, respectively.

| Aminoluciferin | is cleaved by the enzyme |
|---|---|
| (a) | tissue kallikrein EC 3.4.21.35 |
| (b) | leukocyte elastase EC 3.4.21.37 |
| (c) | leukocyte elastase EC 3.4.21.37 |
| (d) | chymotrypsin EC 3.4.21.1 |
| (e) | pankreatic elastase EC 3.4.21.36 |
| (f) | papain EC 3.4.22.2 |
| (g + l) | plasmin EC 3.4.21.7 |
| (h + m) | urokinase EC 3.4.21.6 |
| (i) | thiolproteinase: |
| | cathepsin B EC 3.4.22.1 |
| | cathepsin L EC 3.4.22.15 |
| | cathepsin H EC 3.4.22.16 |
| | ficin EC 3.4.22.3 |
| | bromoalain EC 3.4.22.4 |
| (j) | leukocyte elastase EC 3.4.21.37 |
| | cathepsin G EC 3.4.21.20 |
| (k) | plasma kallikrein EC 3.4.21.34 |
| (n) | trypsin EC 3.4.21.4 |
| (o) | thrombin EG 3.4.21.5 |

For the HPLC purification mentioned above the following mixture is used as mobil phase which consists of a) 0.05 mol/l ammonium acetate in water, pH=8.0
b) methanol used in a volume ratio a:b of 40%:60% to 50%:50%, for instance 42%a:58%b.

We claim:

1. D-aminoluciferin derivatives of the general formula I

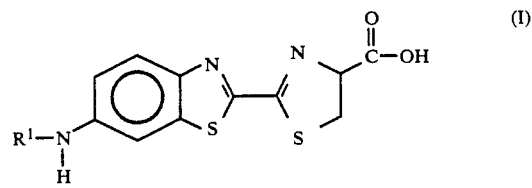

wherein
$R^1$ represents a L-amino acid or peptide radical having up to 10 L-amino acid moieties said radical being bound via the (terminal) carboxyl group in the form of an amide and the free amino group thereof is optionally be protected by a common protecting group, or wherein $R^1$ represents a monosaccharide or disaccharide radical.

2. Luciferin derivatives according to claim 1 of the general formula I wherein the amino acid radicals or the amino acid moieties, respectively, are derived from naturally occurring amino acids.

3. Aminoluciferin derivatives according to claim 1 of the general formula I wherein the amino acid radical $R^1$ corresponds to the general formula II

wherein
$R^3$ is a hydrogen atom or a common protecting group and
$R^2$ is —H, —$CH_3$, —$CH_2OH$, —$CH(OH)CH_3$, —$CH(CH_3)_2$, —$CH_2CH(CH_3)_2$, —$CH(CH_3)CH_2CH_3$, —$CH_2COOH$, —$CH_2CONH_2$, —$CH_2CH_2COOH$, —$CH_2CH_2CONH_2$, —$CH_2CH_2CH_2CH_2NH_2$, —$CH_2C_6H_4OH$, —$CH_2C_6H_5$,

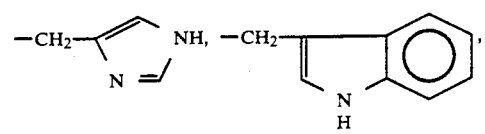

—$CH_2SH$, —$CH_2CH_2CH_2$—NH—C(=N-H)—$NH_2$ or —$CH_2CH_2SCH_3$ steht, or wherein the group of the general formula II is a corresponding prolin or hydroxy prolin radical.

4. Aminoluciferin derivatives according to claim 3 of the general formula I wherein
$R^2$ is —$CH_2C_6H_5$, —$CH_2CH_2CH_2$—NH—C(=N-H)—$NH_2$, —$CH_2C_6H_4OH$, —$CH_2CH_2CH_2CH_2NH_2$ or —$CH_3$.

5. Aminoluciferin derivatives according to claim 1 of the general formula I wherein R[1] represents a peptide radical having up to 5 amino acid moieties.

6. Aminoluciferin derivatives according to claim 5 of the general formula I wherein the free amino group or the free amino groups of the radical R[1] is (are) protected by a common protecting group.

7. Aminoluciferin derivatives according to claim 6 of the formula I wherein the protecting group is an acetyl, benzoyl, tosyl, benzyloxycarbonyl, tert.-butyloxycarbonyl, succinyl or methoxysuccinyl group.

8. Aminoluciferin derivatives according to claim 1 of the general formula I wherein the free amino group or the free amino groups of the radical R[1] is (are) protected by a common protecting group.

9. A composition for detecting enzyme activity which comprises at least one aminoluciferin derivative of claim 1 contained in a buffered aqueous solution.

10. An assay method for an active enzyme which comprises contacting an aqueous solution of said enzyme with a compound of formula (I) of claim 1, detecting the D-aminoluciferin produced, and calculating the enzyme concentration.

11. A method according to claim 10 wherein the D-aminoluciferin is detected by bioluminescence.

12. A method according to claim 10 wherein the enzyme concentration ranges from about 10 to 100 fg.

13. A method according to claim 10 wherein, in the compound of formula (I), the protecting group $R_1$ is selected from the group consisting of acetyl, benzoyl, tosyl, benzoloxycarbonyl, tert.-butyloxycarbonyl, succinyl, and methoxysuccinyl.

* * * * *